(12) United States Patent
Fischmann T.

(10) Patent No.: US 9,080,342 B2
(45) Date of Patent: Jul. 14, 2015

(54) SUCTIONING DEVICE FOR TRAVELLING A TANK BOTTOM

(71) Applicant: Crystal Lagoons (Curacao) B.V., Curacao (NL)

(72) Inventor: Fernando Fischmann T., Santiago (CL)

(73) Assignee: Crystal Lagoons (Curacao) B.V., Curacao (NL)

( * ) Notice: Subject to any disclaimer, the term of this patent is extended or adjusted under 35 U.S.C. 154(b) by 0 days.

(21) Appl. No.: 13/886,615

(22) Filed: May 3, 2013

(65) Prior Publication Data

US 2013/0240432 A1    Sep. 19, 2013

Related U.S. Application Data

(62) Division of application No. 12/937,505, filed as application No. PCT/US2009/036809 on Mar. 11, 2009.

(30) Foreign Application Priority Data

Dec. 24, 2008  (CL) .................................. 3900-2008

(51) Int. Cl.
   *C02F 1/00* (2006.01)
   *C02F 1/52* (2006.01)
   (Continued)

(52) U.S. Cl.
   CPC .. *E04H 4/12* (2013.01); *C02F 9/00* (2013.01); *E04H 4/1209* (2013.01);
   (Continued)

(58) Field of Classification Search
   CPC ........ C02F 1/5281; C02F 1/52; C02F 1/5236; C02F 1/36; C02F 1/001; C02F 1/56; C02F 9/00; C02F 2103/007; C02F 2103/42; E04H 4/1272; E04H 4/1636; E04H 4/1654; E04H 4/1663; E04H 4/1209; E04H 4/1645; E04H 4/12; B01D 24/14; A61M 1/3633; B08B 3/02; A47L 9/2842; A47L 9/362
   USPC ............ 210/738, 712, 167.1, 167.13, 167.15, 210/167.16, 257.1; 15/1.7, 319, 327; 134/56 R
   See application file for complete search history.

(56) References Cited

U.S. PATENT DOCUMENTS 2,071,520 A    2/1937   Harrison
2,141,811 A   12/1938   Everson
(Continued)

FOREIGN PATENT DOCUMENTS

CN    1256250    6/2000
CN    102092824  6/2011
(Continued)

OTHER PUBLICATIONS

Fischmann Torres UY30184 (A1), May 31, 2007, Machine Translation "Process to obtain water bodies larger than 15,000 m3 for recreational use with color, transparency and cleanness swimming pools or tropical seas at low cost".*
(Continued)

*Primary Examiner* — Nam Nguyen
*Assistant Examiner* — Nader Hossaini
(74) *Attorney, Agent, or Firm* — Merchant & Gould P.C.

(57) ABSTRACT

The present invention comprises an efficient filtration process of water from a tank, where the filtration is performed over a small volume of water and not on the totality of the water from the tank; the process comprises the following steps: (a) emitting ultrasonic waves in the tank; (b) adding a flocculant agent to the water; (c) covering the tank bottom with a suctioning device which suctions a water flow with flocculated particles, discharging to a collecting effluent line; (d) filtering the effluent flow of the suctioning device from said collecting effluent line; and (e) returning the filtered flow to the tank. The present invention additionally comprises a suctioning device used in said efficient filtration process.

9 Claims, 9 Drawing Sheets

(51) Int. Cl.

| | | |
|---|---|---|
| *E04H 4/16* | (2006.01) | |
| *A47L 5/00* | (2006.01) | |
| *B01D 21/01* | (2006.01) | |
| *E04H 4/12* | (2006.01) | |
| *C02F 9/00* | (2006.01) | |
| *B08B 3/02* | (2006.01) | |
| *A47L 9/28* | (2006.01) | |
| *A61M 1/36* | (2006.01) | |
| *C02F 1/36* | (2006.01) | |
| *C02F 1/56* | (2006.01) | |
| *C02F 103/00* | (2006.01) | |
| *C02F 103/42* | (2006.01) | |

(52) U.S. Cl.
CPC ........... *E04H 4/1645* (2013.01); *E04H 4/1654* (2013.01); *A47L 9/2842* (2013.01); *A61M 1/3633* (2013.01); *B08B 3/02* (2013.01); *C02F 1/001* (2013.01); *C02F 1/36* (2013.01); *C02F 1/52* (2013.01); *C02F 1/56* (2013.01); *C02F 2103/007* (2013.01); *C02F 2103/42* (2013.01)

(56) References Cited

U.S. PATENT DOCUMENTS

| | | | |
|---|---|---|---|
| 2,314,767 A | 3/1943 | Burrell | |
| 2,646,889 A | 7/1953 | August | |
| 2,923,954 A | 2/1960 | Babcock | |
| 3,132,773 A | 5/1964 | Hampton | |
| 3,247,053 A | 4/1966 | Hodge | |
| 3,266,631 A | 8/1966 | Snaper | |
| 3,317,925 A | 5/1967 | Vance | |
| 3,361,150 A | 1/1968 | Horner | |
| 3,412,862 A | 11/1968 | Chaplin | |
| 3,406,416 A | 12/1968 | Presby et al. | |
| 3,419,916 A | 1/1969 | Schankler | |
| 3,470,091 A | 9/1969 | Budd et al. | |
| 3,540,274 A | 11/1970 | Shore | |
| 3,641,594 A | 2/1972 | Hough | |
| 3,660,957 A | 5/1972 | Schankler | |
| 3,695,434 A | 10/1972 | Whitten, Jr. | |
| 3,748,810 A | 7/1973 | Mattingly | |
| 3,788,982 A | 1/1974 | Zsoldoes, Jr. et al. | |
| 3,844,760 A | 10/1974 | Nelson | |
| 3,887,666 A | 6/1975 | Heller et al. | |
| 3,949,442 A * | 4/1976 | Chandler | 15/1.7 |
| 3,950,809 A | 4/1976 | Schatzmann | |
| 4,055,491 A | 10/1977 | Porath-Furedi | |
| 4,060,575 A | 11/1977 | Uhlirsch et al. | |
| 4,063,419 A | 12/1977 | Garrett | |
| 4,090,266 A | 5/1978 | Price | |
| 4,100,641 A | 7/1978 | Pansini | |
| 4,117,683 A | 10/1978 | Rasmussen | |
| 4,119,535 A | 10/1978 | White | |
| 4,129,904 A * | 12/1978 | Pansini | 4/490 |
| 4,176,058 A | 11/1979 | Grobler | |
| 4,254,525 A | 3/1981 | Combest | |
| 4,254,818 A | 3/1981 | Melamed | |
| 4,263,759 A | 4/1981 | Miller | |
| 4,304,022 A | 12/1981 | Sommer | |
| 4,306,967 A | 12/1981 | Trautwein | |
| 4,338,697 A | 7/1982 | Broadwater | |
| 4,343,696 A | 8/1982 | Hung | |
| 4,402,101 A * | 9/1983 | van Zyl | 15/1.7 |
| 4,464,215 A | 8/1984 | Cogliano | |
| 4,519,914 A | 5/1985 | Etani | |
| 4,548,371 A * | 10/1985 | Dempsey | 244/13 |
| 4,572,767 A | 2/1986 | McCord | |
| 4,581,075 A | 4/1986 | St. Martin | |
| 4,640,784 A | 2/1987 | Cant | |
| 4,652,378 A | 3/1987 | Marikovsky et al. | |
| 4,692,956 A | 9/1987 | Kassis | |
| 4,752,740 A | 6/1988 | Steininger | |
| 4,767,511 A | 8/1988 | Aragon | |
| 4,768,532 A | 9/1988 | Johnson | |
| 4,776,053 A | 10/1988 | Kiraly | |
| 4,835,810 A | 6/1989 | Hugo | |
| 4,849,024 A | 7/1989 | Supra | |
| 4,880,547 A | 11/1989 | Etani | |
| 4,889,622 A | 12/1989 | Newcombe-Bond | |
| 4,909,266 A | 3/1990 | Massa | |
| 4,931,187 A | 6/1990 | Derham et al. | |
| 4,948,296 A | 8/1990 | Salter | |
| 4,952,398 A | 8/1990 | Tapin | |
| 5,028,321 A | 7/1991 | Stone et al. | |
| 5,039,427 A | 8/1991 | Conover | |
| 5,106,229 A | 4/1992 | Blackwell | |
| 5,107,872 A | 4/1992 | Meincke | |
| 5,108,514 A | 4/1992 | Ksiner | |
| 5,143,623 A | 9/1992 | Kroll | |
| 5,164,094 A | 11/1992 | Stuckart | |
| 5,172,445 A | 12/1992 | Chandler | |
| 5,245,723 A | 9/1993 | Sommer | |
| 5,268,092 A | 12/1993 | Eden | |
| 5,293,659 A | 3/1994 | Rief et al. | |
| 5,337,434 A | 8/1994 | Erlich | |
| 5,342,570 A | 8/1994 | Ledoux et al. | |
| 5,346,566 A | 9/1994 | White | |
| 5,398,361 A | 3/1995 | Cason | |
| 5,422,014 A | 6/1995 | Allen et al. | |
| 5,454,129 A | 10/1995 | Kell | |
| 5,569,371 A | 10/1996 | Perling | |
| 5,616,239 A | 4/1997 | Wendell et al. | |
| 5,662,940 A | 9/1997 | Hight et al. | |
| 5,782,480 A * | 7/1998 | Phillips | 280/282 |
| 5,802,631 A | 9/1998 | Friedman | |
| 5,842,243 A | 12/1998 | Horvath et al. | |
| 5,985,156 A | 11/1999 | Henkin et al. | |
| 6,017,400 A | 1/2000 | Clark et al. | |
| 6,149,819 A | 11/2000 | Martin et al. | |
| 6,224,826 B1 | 5/2001 | Katakura et al. | |
| 6,228,272 B1 | 5/2001 | Gola | |
| 6,231,268 B1 | 5/2001 | Hausenbauer | |
| 6,280,639 B1 | 8/2001 | Ortiz | |
| 6,284,144 B1 | 9/2001 | Itzhak | |
| 6,303,038 B1 | 10/2001 | Sanders et al. | |
| 6,317,901 B1 | 11/2001 | Corpuel | |
| 6,409,926 B1 | 6/2002 | Martin | |
| 6,419,840 B1 | 7/2002 | Meincke | |
| 6,444,176 B1 | 9/2002 | Yoshinaga et al. | |
| 6,539,573 B1 | 4/2003 | Caccavella | |
| 6,620,315 B2 | 9/2003 | Martin | |
| 6,896,799 B2 * | 5/2005 | Ohanian | 210/167.23 |
| 7,163,619 B2 | 1/2007 | Wang | |
| 7,189,314 B1 | 3/2007 | Pace et al. | |
| 7,252,843 B2 | 8/2007 | Moore et al. | |
| 7,820,055 B2 | 10/2010 | Fischmann Torres | |
| 7,832,959 B1 | 11/2010 | Groen et al. | |
| 7,862,712 B2 | 1/2011 | Tak | |
| 8,153,010 B2 | 4/2012 | Duarte et al. | |
| 8,388,837 B2 | 3/2013 | Tormaschy et al. | |
| 8,524,088 B2 | 9/2013 | Arbogast et al. | |
| 2002/0117430 A1 | 8/2002 | Navarro et al. | |
| 2003/0046933 A1 | 3/2003 | Moss et al. | |
| 2003/0091467 A1 | 5/2003 | Kmec et al. | |
| 2003/0094421 A1 | 5/2003 | Gargas | |
| 2003/0228195 A1 | 12/2003 | Mizutani | |
| 2004/0025269 A1* | 2/2004 | Pichon | 15/1.7 |
| 2004/0129644 A1 | 7/2004 | Unhoch | |
| 2004/0211450 A1* | 10/2004 | Stoltz | 134/166 R |
| 2004/0217326 A1 | 11/2004 | Souter et al. | |
| 2004/0226896 A1 | 11/2004 | Lovestead et al. | |
| 2005/0009192 A1 | 1/2005 | Page | |
| 2005/0016906 A1 | 1/2005 | Gettman | |
| 2005/0063782 A1 | 3/2005 | Stoecker et al. | |
| 2005/0145552 A1 | 7/2005 | Sheets | |
| 2005/0194322 A1 | 9/2005 | Palmer | |
| 2005/0207939 A1 | 9/2005 | Roussi et al. | |
| 2006/0054568 A1 | 3/2006 | Jones et al. | |
| 2006/0169322 A1 | 8/2006 | Torkelson | |
| 2006/0174430 A1 | 8/2006 | Pareti | |
| 2007/0059562 A1 | 3/2007 | Hattori et al. | |
| 2007/0181498 A1 | 8/2007 | Kaas | |

(56) References Cited

U.S. PATENT DOCUMENTS

| | | |
|---|---|---|
| 2007/0181510 A1 | 8/2007 | Harvey et al. |
| 2008/0116142 A1 | 5/2008 | Fischmann Torres |
| 2008/0295615 A1 | 12/2008 | Sihalla |
| 2009/0050572 A1 | 2/2009 | McGuire et al. |
| 2009/0087549 A1 | 4/2009 | Zhou et al. |
| 2010/0320147 A1 | 12/2010 | McGuire et al. |
| 2011/0009019 A1 | 1/2011 | Neira et al. |
| 2011/0061194 A1 | 3/2011 | Fischmann Torres |
| 2011/0062067 A1 | 3/2011 | Fischmann Torres |
| 2011/0132815 A1 | 6/2011 | Angellili et al. |
| 2011/0210076 A1 | 9/2011 | Fischmann Torres |

FOREIGN PATENT DOCUMENTS

| | | |
|---|---|---|
| DE | 2 141 460 | 2/1973 |
| DE | 38 44 374 | 7/1990 |
| DE | 19515428 | 11/1996 |
| DE | 297 16 994 | 1/1998 |
| DE | 198 14 705 | 10/1998 |
| DE | 198 60 568 | 12/1998 |
| DE | 10 2010 019 510 | 11/2011 |
| EP | 0 352 487 | 1/1990 |
| EP | 0 468 876 | 1/1992 |
| EP | 0 483 470 | 5/1992 |
| EP | 1 420 130 | 5/2004 |
| EP | 168 85 62 | 8/2006 |
| ES | 200 14 29 | 5/1998 |
| FR | 2 544 005 | 10/1984 |
| FR | 2 668 527 | 4/1992 |
| FR | 2 685 374 | 6/1993 |
| FR | 2 740 493 | 4/1997 |
| FR | 2 785 898 | 5/2000 |
| GB | 1494005 | 12/1977 |
| GB | 2045606 | 11/1980 |
| GB | 2 243 151 | 10/1991 |
| JP | 59-012287 | 1/1984 |
| JP | 59-222294 | 12/1984 |
| JP | 4-115008 | 4/1992 |
| JP | 5-220466 | 8/1993 |
| JP | 04073612 | 8/1993 |
| JP | 5-261395 | 10/1993 |
| JP | 7-310311 | 11/1995 |
| JP | 3026643 | 1/1996 |
| JP | 10-169226 | 6/1998 |
| JP | 2001-3586 | 1/2001 |
| JP | 2001-9452 | 1/2001 |
| JP | 2002-90339 | 3/2002 |
| JP | 2002-282860 | 10/2002 |
| JP | 2003-190989 | 7/2003 |
| JP | 2003-200173 | 7/2003 |
| JP | 2004-958 | 1/2004 |
| JP | 2005-288392 | 10/2005 |
| JP | 2006-68624 | 3/2006 |
| JP | 2007-500073 | 1/2007 |
| JP | 2011-5463 | 1/2011 |
| KR | 20-0162956 | 9/1999 |
| TW | 432013 | 8/1987 |
| TW | 482186 | 12/1990 |
| WO | WO 8101585 | 6/1981 |
| WO | WO 9848132 | 10/1998 |
| WO | WO 03/010388 | 2/2003 |
| WO | WO 2006/069418 | 7/2006 |
| WO | WO 2007/029277 | 3/2007 |
| WO | WO 2007/059562 | 5/2007 |
| WO | WO 2009/114206 | 9/2009 |
| WO | WO 2010/074770 | 7/2010 |

OTHER PUBLICATIONS

Fischmann Torres UY30184 (A1), May 31, 2007—Machine Translation "Process to obtain water bodies larger than 15,000 m3 for recreational use with color, transparency and cleanness swimming pools or tropical seas at low cost."
African Regional Intellectual Property Organization (ARIPO) report for corresponding application No. AP/P/2007/004242 dated Dec. 7, 2010.
Ambient Water Quality Criteria for Bacteria—1986, Jan. 1986, US EPA, EPA440/5-84-002, p. 16.
Chilean Examiner's report from Application No. 3900-08 issued Aug. 31, 2009.
Final Office Action mailed Nov. 28, 2011 from U.S. Appl. No. 13/076,151.
Non-Final Office Action mailed Apr. 19, 2012 from U.S. Appl. No. 13/195,695.
Non-Final Office Action mailed Apr. 24, 2012 from U.S. Appl. No. 13/136,474.
Non-Final Office Action mailed Apr. 3, 2012 from U.S. Appl. No. 13/136,458.
Non-Final Office Action mailed Jul. 19, 2011 from U.S. Appl. No. 13/076,151.
Restriction Requirement Office Action mailed Jan. 13, 2012 from U.S. Appl. No. 13/136,474.
Restriction Requirement Office Action mailed Jan. 13, 2012 from U.S. Appl. No. 13/136,458.
European Search Report from European Application No. 07 07 5995 mailed Mar. 9, 2010.
International Search Report and Written Opinion for International Application No. PCT/US2011/051229 mailed Feb. 8, 2012.
International Search Report and Written Opinion for International Application No. PCT/US2011/051236 mailed Jan. 26, 2012.
International Search Report and Written Opinion for International Application No. PCT/US2011/051244 mailed Jan. 25, 2012.
International Search Report mailed May 6, 2009, in co-pending related PCT Application No. PCT/US2009/036809.
Japanese Office Action for corresponding application No. 2007-299975 dated May 31, 2011—translation provided.
Norwegian Search Report from Norwegian Application No. 20075880 dated Feb. 4, 2010.
Office Action for corresponding U.S. Appl. No. 12/884,842 mailed Mar. 1, 2011.
Office Action for corresponding U.S. Appl. No. 12/884,872 mailed Mar. 1, 2011.
Panama Search Report from Panama Application No. 87176-01 dated Mar. 17, 2010.
Panama Search Report from Panama Application No. 88509-01 dated Oct. 7, 2010.
Peruvian Technical Report for corresponding application No. 000244-2007 dated Sep. 2, 2010—translation provided.
Second Singapore Office Action for corresponding application No. 200717963-3 dated Dec. 23, 2010.
Singapore Office Action for corresponding application No. 200717963-3 dated Dec. 23, 2010.
World Health Organization: Guidelines for safe recreational waters. vol. 2. Swimming pools and similar recreational water environments. Switzerland. Jun. 27, 2006 ISBN 92-4-154680-8 Chapter 4.
World Health Organization: Guidelines for safe recreational waters. vol. 2. Swimming pools and similar recreational water environments. Switzerland. Jun. 27, 2006 ISBN 92-4-154680-8 Chapter 5.
Eurasian Office Action for corresponding application No. 201001477/31 and response to Office Action dated Apr. 2, 2013 with English Translation.
Communication from EPO for corresponding application No. 09835402.0 dated Jan. 30, 2013.
Response filed for EP 09835402.0 dated Jul. 23, 2013. (11 pages).
Response filed for EP 09835402.0 dated Aug. 14, 2013. (9 pages).

* cited by examiner

SUCTIONING DEVICE FOR TRAVELLING A TANK BOTTOM

This application is a Divisional of Ser. No. 12/937,505, filed 3 Jan. 2011, which is a National Stage of PCT/US2009/036809, filed 11 Mar. 2009, which claims benefit of Ser. No. 3900-2008, filed 24 Dec. 2008 in Chile and which applications are incorporated herein by reference. To the extent appropriate, a claim of priority is made to each of the above disclosed applications.

FIELD OF THE INVENTION

The present invention describes a filtration process for water in large tanks, such as fountains, reflecting pools, pools and lakes, with low investment and operating costs.

BACKGROUND

When water is placed into recreational or ornamental tanks, the water often becomes cloudy in spite of the good quality and low levels of suspended solids in the water source. The environment adds dust, soil, organic matter, etc., to the tank. However, the main source of suspended particles causing water cloudiness is often the inevitable growth of micro organisms, especially micro algae which are broadly spread in nature and which find suitable conditions of life in these aquatic media.

Algae are a varied group of plants that are found in a wide range of environmental habitats. They are photosynthetic plants containing chlorophyll, which have very simple reproductive structures and their tissues are not differentiated in roots, stems or real leaves. The average single size of microscopic single-cell alga is about 1 μm. Algae are found around the world and they can cause problems in tanks.

Exterminating algae is a long felt problem. Algae are single-cell plant organisms which reproduce under the light of the sun. They are present in vegetation, air, soil and water. Their microscopic spores are continuously inserted in tanks and other bodies of water by wind, sand storms, rain, etc. They grow rapidly in stagnant water when they are exposed to sun light and temperatures above 4° C. They can generate mud and/or odors. They can interfere in suitable filtration and considerably increase the chlorine demand in public pools. The presence of phosphates and nitrates in water promotes their growth.

Planktonic algae are single celled microscopic plants that float freely in water. When these plants are extremely abundant or they "bloom", they make the water in tanks turn green. Less frequently, they can turn the water into other colours, including yellow, grey, brown or red.

SUMMARY

According to one aspect of the invention, there is provided a process for filtering water in tanks. The filtration process is performed over a small water volume and not over an entire tank of the water. The process includes emitting ultrasonic waves in the tank, adding a flocculant agent to the water, covering a tank bottom with a suctioning device which suctions a water flow with flocculated particles to produce a suctioning device effluent, discharging the suctioning device effluent to an effluent collecting line, filtering the suctioning device effluent flow from said effluent collecting line to produce a filtered flow, and returning the filtered flow to the tank.

According to another aspect of the invention, there is provided a suctioning device for travelling a tank bottom with water. The suctioning device suctions a water flow with flocculated particles in order to accomplish filtration of the water of said tank. The suctioning device includes a structural frame having a means of coupling to a pump system, a means of wheeling with a horizontal axle for moving around the tank bottom, a means of rotative sliding with a vertical axle for adjacent displacement to walls of the tank, a means of suctioning including a plurality of suction lines, a means of cleaning, and a means of pivoting between the means of wheeling and the structural frame.

It is to be understood that both the foregoing general description and the following detailed description are exemplary and explanatory and are intended to provide further explanation of the invention as claimed.

BRIEF DESCRIPTION OF FIGURES

The following drawing figures, which form a part of this application, are illustrative of embodiments systems and methods described below and are not meant to limit the scope of the invention in any manner, which scope shall be based on the claims appended hereto.

DESCRIPTION OF THE INVENTION

The present invention describes an efficient and economic filtration process for water from tanks, such as fountains, reflecting pools, public swimming pools and artificial lakes. The suspended solids in water precipitate by means of the synergic action of flocculant agents and ultrasonic waves, and they are then collected on the bottom by suction with a suctioning device. The outlet of said suctioning device is then filtered and returned to the tank, eliminating the turbidity from all of the water in the tank and filtering only a very small flow, which corresponds to the outlet from the suctioning device, compared to the flows that are required in traditional filtration systems which filter all of the tank water. Additionally, a necessary suctioning device for accomplishing the process of the present invention is described.

As noted above, water placed into tanks may become cloudy due to a number of factors. In order to eliminate suspended solids such as algae, dust, organic matter, etc., from tanks, filtration systems are usually used. Filtration is a technique consisting in passing a mixture of solids and fluids, gases or liquids, through a porous or filtering media that can be part of a device called a filter, where most of solid components of the mixture are removed.

The uses of filtration process are diverse and are found in many areas of human activity, domestic life and industry where industrial process that require chemical engineering techniques are particularly important.

Filtration has been developed along with human evolution, receiving more theoretical attention since the 20$^{th}$ Century. The classification of filtration process and equipment is diverse and, in general, classification categories are not mutually exclusive with each other.

The variety of filtration devices and filters is as wide as types of available porous materials for its use as filtering media and particular conditions in every application: from simple devices, such as domestic coffee filters or filtration funnels for laboratory separation, to huge complex systems that are highly automated, such as those used in the petrochemical industry and refining for high value catalyst recovery, or drinking water treatment systems for urban supply.

Filtration is a mechanical or physical operation used for the separation of solids in fluids (such as liquids or gases), in which a filtering media is inserted and the fluid can flow across the filtering media, but the solids (or at least a part of them) are retained. Usually, the separation is considered incomplete and depends of the pore size and media thickness as well as the mechanics that take place during the filtration. Generally, in a filtration process the filtering media has several layers, but other mechanisms are also involved such as direct interception, diffusion and centrifugal action, in which the particles are not able to follow the winding channels of the filtering media through which the flow lines are passing and they remain withheld in the fibers of the filtering media.

There are two main filtration techniques:
Frontal filtration, which is the best known passes the fluid perpendicularly through the surface of the filtering media. This technique is used, for example, in domestic coffee filters. Particles are retained in the filter; this technique is limited by particle accumulation in the filtering media surface, which is finally blocked;
Tangential filtration, on the other hand, passes the fluid tangentially through the filtering media surface. It is the fluid's pressure which allows itself cross the filter. In this case, the particles remain in tangential flow and the filter's blocking is slower. However, this technique is only used for very small particles, from one nanometre (nm) to one micrometer (μm).

Additionally, the types of filtration can be classified according to the pore size of the filtering media:
clarifying filtration: when the pore diameter is from 10 to 450 μm;
sterilizing filtration: when the pore diameter is more than 0.22 μm;
micro filtration: when the pore diameter is from 10 nm to 10 μm;
ultra filtration: when the pore diameter is from 1 to 10 nm;
reverse osmosis: when the pore diameter is from 0.1 to 1 nm.

The efficiency of filtration depends on a set of variables, such as pressure, filtering media, viscosity, temperature, particle size and concentration.

In general, if the increase in pressure leads to a significant increase in the flow or filtration rate, this is a sign of granulated cake formation. However, for thick or very fine cakes, an increase in pumping pressure does not lead to a significant increase of the filtering flow. In other cases, the cake is characterized by a critical pressure above which the filtration rate is even decreased. In practice, operating at a constant rate, starting at low pressure, is preferred, although because of the widespread use of centrifugal pumping systems, the regular conditions are variable pressure and flow.

Theory points out that, besides considering the characteristics of the filtering media, the mean flow is inversely proportional to the amount of cake and directly proportional to the square of the area to be filtered. As a result of these two variables, for the same amount of fluid to be filtered, it will be noted that its flow is inversely proportional to the square thickness of the cake at the end of the process. This observation entails that maximum productivity is theoretically achieved with those cakes with a very thin thickness, whose resistance exceeds the resistance of the filtering media. However, other factors, such as the time to regenerate the cake, its discharge difficulty and the cost of a wider filtering surface explain that in practice it is preferred to work under conditions with thicker cakes.

The filtering flow rate, at any time, is inversely proportional to the filtering viscosity.

As the filtering temperature is increased, its viscosity is decreased and, hence, the filtering flow rate is increased.

The effect of particle size on cake resistance and film is remarkable. Even small modifications of the exchange of particles affect the coefficient in the equation for cake resistance and major changes affect compressibility.

For the reasons mentioned above, filtration is not a simple process, specially when large flows are filtered.

In ornamental and recreational tanks, such as public pools and fountains, diatomaceous, cartridge and sand systems are used, the latter being the most common systems.

Sand filters are the elements that are most used in filtering water with low or medium charges of contaminants, requiring particle removal of up to 20 μm of size. The suspended particles that are carried by water are retained when they pass over a filtering bed of sand. Once the filter is loaded with impurities, reaching a predetermined charge loss, the filter can be regenerated by upstream flushing.

The filtration quality depends on various parameters, among others, the shape of the filter, the height of the filtering bed, the characteristics and granulometry of filtering mass, the filtration rate, etc.

These filters can be manufactured with polyester resins and glass fiber, suitable for river and sea water filtration because of their complete resistance to corrosion. Also stainless steel and carbon steel for embodiments in which a better resistance to pressure is required.

The use of filtration systems in ornamental and recreational tanks such as reflecting pools and swimming pools is widely spread worldwide, however, when the size of these tanks is increased two problems emerge that limit their scale.

The first limitation is that of high investment and operating costs. In fact, in the world there are very few recreational tanks with filtered water of more than 2,500 m$^3$ (the volume of an Olympic pool) and those closest to these volumes have high operating costs.

For example, if is a matter of a pool in a residential condominium with a volume of 9,000 m$^3$, then a filtration rate of 416 l/s is required to meet the recommendations of sanitary regulation for filtration in public pools. These operating volumes are unmanageable for this type of building project because of the initial investment, the area occupied by the filtration systems, the complexity and, especially, the operating costs.

However, there is a second problem which complicates filtration in large bodies of water and it is related to the difficulty of homogenously filtering the entire volume of water. In an ordinary pool or fountain, one point of suction and one point of discharge is enough to achieve a relative homogenously filtration of all of the water. As the body of water increases in volume, the influence of the suction point is limited to the surrounding area and it has no effect on the entire volume. This implies that a complex and costly network of pipes with a large number of suction and discharge points must be planned. This type of system has high pressure losses and also generates short circuits in the flow of filtrate, i.e., the same water is filtered several times, decreasing the efficiency of the system.

For the reasons mentioned above, it is not economically viable and very inefficient to maintain large water bodies with filtration systems, and therefore there are no large filtered tanks for ornamental or recreational use in the world.

In the state of the art, there is Chilean Patent Registration Number CL 43,534, which is oriented toward obtaining large bodies of water for recreational use, which describes a process for obtaining (i.e., installing and maintaining) large volumes or bodies of water for recreational purposes, such as lakes and pools with excellent coloration, high transparency and cleanliness similar to those of pools or tropical seas with low cost, especially for bodies of water larger than 15,000 $m^3$. The present invention defines structural features such as skimmers for oil elimination, water collection systems, building details, types and colors of liners, circulation systems and additive injection, requirements for supplying water, pH measuring, addition of salts, use of algaecides and flocculants, change rates of fresh water, additives and oxidation processes, and a suctioning vehicle driven by a boat.

In Patent, CL 43,534, an open system for water circulation is used, therefore no way to retrieve water is considered and no type of filtration is used. Nor is the problem of biofilm solved that is formed on the walls and bottom of the tank, which is eliminated manually in small bodies, but which is impossible to accomplish in larger tanks.

The aim of the present invention is different from that of Patent CL 43,534 and, on the contrary, in the present patent application, a low cost filtration system is defined that allows for the recovery of water without filtering the entire tank water, as occurs with expensive water filtration systems in tanks known to date, nor discarding the water from the suction system as occurs in the patent mentioned above, which implies larger uses of water and eventually the discharge of water with sediments to natural flows.

In Patent CL 43,534, the water is discarded and it does not comprise a filtration system, therefore the efficiency of the suction system and, obviously, the filtration itself are not critical. However, suctioning the bottom of larger tanks in a efficient way using low water flows (a critical point when the outflow must be filtered) is a complex issue because the suctioner must pass at high speed in order to cover the large surfaces and therefore a sediment cloud is lifted which makes the water cloudy and decreases the system efficiency. In turn, there are economical and regulatory constraints in using large amounts of flocculants because of the costs, given the large volumes of water involved and sanitary restrictions. On the other hand, the characteristics of this sediment are not suitable for efficient filtration.

A solution has been found for the problem of economic water filtration for larger tanks, without the need of filtering the entire volume of water as occurs with the present systems, with the development and verification of the joint use of flocculant agents and ultrasound, which generates dispersed floccules at the bottom of the tank, separated from each other and easily suctionable by a suctioning device specially designed which can cover large surfaces in a short time and then filtered with high efficiency, because of the filtrate quality, with a simple device such as a sand filter or another small and economic filter available on the market using small concentrations of flocculants.

The application of ultrasound in larger tanks allows a very effective and easy suction with the suctioning device, not only due to the formation of large and dispersed floccules with easy suctioning and filtering, but also allows the application of ultrasound that permits controlling the growth of biofilm in tanks and eliminating the environment in which the algae stick to the walls and bottom of the tanks. The biofilm is comprised of layers of bacteria formed on host surfaces, creating points of adherence for algae that are hard to dislodge from the tank's surfaces. For these cases, the ultrasound waves prevent the formation of the base layer of biofilm to avoid having the majority of planktonic floating bacteria from becoming sessile bacteria with strongly adhesive capability to grow on a surface. The base layer of biofilm begins to form as fast as 20 minutes to 3 hours after cleaning a surface immersed in a pond.

With the application of ultrasonic waves in the flocculation process, the process of the present invention in fact removes algae cells, particles, dust and turbidity in general from water, significantly improving the flocculation efficiency due to the effect of ultrasound in coagulating flocculants. To achieve a 90% removal in general of algae, particles, dust and turbidity, sonication reduces the amount of flocculants by two thirds. The process of the present invention has the great advantage with respect to the previous way of filtering water from tanks of very low investment and operating costs and high water filtration efficiency.

Indeed, compared to traditional tank filtration systems, excellent results are obtained in the level of water clarity with much lower investment and operating costs, since it uses a synergic system between the suspended particle flocculation and sonication, which is easily suctioned off by the suctioning device due to the formation of large size floccules that are individually fusioned and easy to suction without the presence of biofilms and also efficient filtration due to the quality of sediment by a small, standard, economic filter that is readily available on the market. This is achieved using very low levels of flocculants. Ultimately, filtering only a small percentage of the total water volume corresponding to the outflow from the suctioning device achieves a result that is equal to or better than that with traditional systems that filter the entire body of water.

The present invention provides for an efficient and economic filtration of water from a tank, where the filtration is carried out on a small volume of water and not on the entire tank water, which comprises the following steps:
 a.—emitting ultrasonic waves in the tank;
 b.—adding a flocculant agent to the water;
 c.—covering the tank bottom with a suctioning device, which suctions a water flow with flocculated particles and discharges a collecting line of effluent;
 d.—filtering the effluent flow of the suctioning device from said collecting line of effluent; and
 e.—returning the filtered flow to the tank.

Preferably, in step a) of the present invention the ultrasonic waves are emitted over a period of time from 1 to 24 hours daily with a frequency from 20 to 100 kHz and power in a range from 10 to 45 W.

Preferably, in step a) of the present invention process, the ultrasonic waves are emitted over a period of time from 12 to 24 hours, and more preferably from 20 to 24 hours.

The ultrasonic waves can be emitted by emitter devices. These devices emit ultrasonic waves in radial form in a range of 180° and with a distance of 150 meters of radius, therefore the emitter devices of ultrasonic waves are located below the surface of the water and spaced by a radius in a range from 100 to 150 m, so all the water from the tank receives the emitted ultrasonic waves.

Usually, ultrasonic wave emitters are provided in the tank's rims; however, in case of a tank with a diameter larger than 300 meters, a central island or another central platform can be formed that allows providing emitter devices in the center of the tank, situated so that the entire surface is subjected to ultrasonic waves according to the coverage range of the emitter device used.

The purpose of step a) of the present invention process is:
- to decrease the amount of microalgae, which is the main component of suspended solids in water; making the suctioning process easier and increasing efficiency of subsequent filtration with an ecologic method at low cost which decreases the application of chemical products and maintains the final purpose of low operating cost;
- to eliminate biofilm formation that is usually formed on the walls and bottom of the tank and that is a source of algae growth, which makes the use of the suctioning device more efficient and decreases manual cleaning of the walls, generating a synergic effect;
- to decrease the amount of flocculant and facilitate algae and particle coagulation in general for removal from the bottom with the suctioning device;
- to make the suction with the suctioning device easier due to the synergic effect between ultrasonic waves and flocculant, because this allows obtaining larger floccules with easy suction without generating a suspended particle cloud formed when the suctioning device covers the bottom of the tank;
- to facilitate filtration with the use of simple sand filters without additional flocculation; and
- to eliminate turbidity of the tank water along with the flocculant.

Preferably, in step b) of the process of the present invention, the flocculant agent is an ionic polymer. More preferably, said ionic polymer is a biodegradable cationic polyelectrolyte.

Preferably, in step b) of the process of the present invention, a flocculant agent is added to the tank water, in a concentration from 0.005 to 2 ppm at least once every 6 days, preferably in a concentration from 0.01 to 0.5 ppm at least once every 4 days; more preferably in a concentration from 0.0125 to 0.04 ppm every 24 hours.

Preferably, in step c) of the process of the present invention, the water flow with flocculated particles is in a range from 1 to 30 L/s. More preferably, the water flow with flocculated particles is in a range from 10 to 20 L/s.

On the other hand, in step c) of the present invention, when the tank bottom is covered with the suctioning device, this can be moved by different means of traction such as a boat in the tank surface; a locomotive cart on rails in the tank bottom; a motorized, automated and/or remote-controlled robot; or with a cable and pulley system.

In step d), the water flows are variable depending on the size of the suctioning device, which in turn is related to the volume of the tank. Preferably, in step d) of the process of the present invention, the effluent flow from the suctioning device is filtered in a range of 1 to 30 L/s, more preferably in a range from 10 to 20 L/s.

The effluent flow from the suctioning device is pumped by a mobile pump connected to the suctioning device with a flexible suctioning hose located along the rim on the tank's water surface on a mobile or fixed platform or on a boat. The effluent from the suctioning device is unloaded to a collecting effluent line; from said collecting effluent line water is pumped using a centrifuge pump for filtering, with a flow preferably from 1 to 30 L/s, more preferably with a flow from 10 to 20 L/s; and at a pressure from 100 to 300 kPa (1 to 3 bar) toward the filter. Said filter can be a sand, diatomaceous or cartridge filter according to the effluent flow being suctioned by the suctioning device.

In step e), the filtered water is returned to the tank using a recirculating pump located on the tank's rim and connected with a hose or pipe to a supply line; using injectors the filtered water is returned to the tank from said supply line to finish the recirculating cycle and in this way to conserve the water within the system.

It is important to bear in mind that the aim of the suctioning device is cleaning the tank bottom in the process of the present invention, as occurs with suctioning devices in traditional pools, but also along with the flocculant and ultrasonic emission the traditional filtration system of public swimming pools is totally replaced. In other words, the suctioning device not only eliminates the material naturally situated on the bottom (leaves, branches, soil, etc.), but also all suspended particles and, in the case of public swimming pools, these are eliminated by filtration of the entire water four times a day. In the case of the present invention, the suspended particles become floccules via the ultrasound and flocculant (larger particles easy for suction) and are suctioned by the suctioning device and then filtered, decreasing elimination costs by two orders of magnitude. That is to say, instead of filtering all the water with traditional systems, only the effluent flow from the suctioning device is filtered.

Optionally, the filtrate of the present invention can incorporate the water from surface disposal grooves or outlets (skimmers) in order to eliminate, specifically, a tank water surface layer, which can comprise oils and floating particles. The evacuated flow using the skimmers can be incorporated into the effluent collecting line in order to filter it as in step d) of the present invention, since the skimmers only eliminate a surface water layer with a very low flow, such as from 1 to 5 L/s. This does not affect the yield of economic filters available on the market that are used in the process of the present invention. It is important to point out that, in some traditional filtration systems, the water is incorporated into the filter from the skimmers, but in this case this corresponds to larger flows which are meant to not only eliminate the surface layer, but also filter all of the water. In the process of the present patent, it is a question of filtering only the superficial layer so that flows are filtered in two lower orders of magnitude.

In the present invention, a suctioning device capable of covering large surfaces under the tank water is necessary, such as those capable of covering 1 ha in 3 hours, i.e., capable of advancing with a speed of 0.93 m/s; said suctioning device was not found on the market, therefore a suctioning device was especially designed to perform step c) of the process of the present invention; said device covers at least a surface 100 times larger than the tank bottom in the same period of time, better than any other existing device.

As seen in FIGS. 4 to 11, the suctioning device used in step c) of the process of the present invention essentially comprises a structural frame (10); a means of coupling (20) to the pump system; means of wheeling (30) with horizontal axis for displacement over the tank bottom; a means of rotative sliding (40) with vertical axis for displacement surrounding the tank walls; a means of suctioning (50) which comprises a plurality of suctioning lines that suction a water flow with flocculated particles from the tank bottom towards the means of coupling (20); means of cleaning (60) which comprise a brush line; a means of pivoting (70) between the means of wheeling (30) and a structural frame (10) for adapting the suctioning device to the prominences in the tank bottom; the structural frame (10) comprises a means of pivotable subjection (80) for attaching to a means of traction, such as a remote-controlled robotized submarine; and a means of fastening (90) between the means of suctioning (50), the means of cleaning (60) and the structural frame (10).

Figure 5:
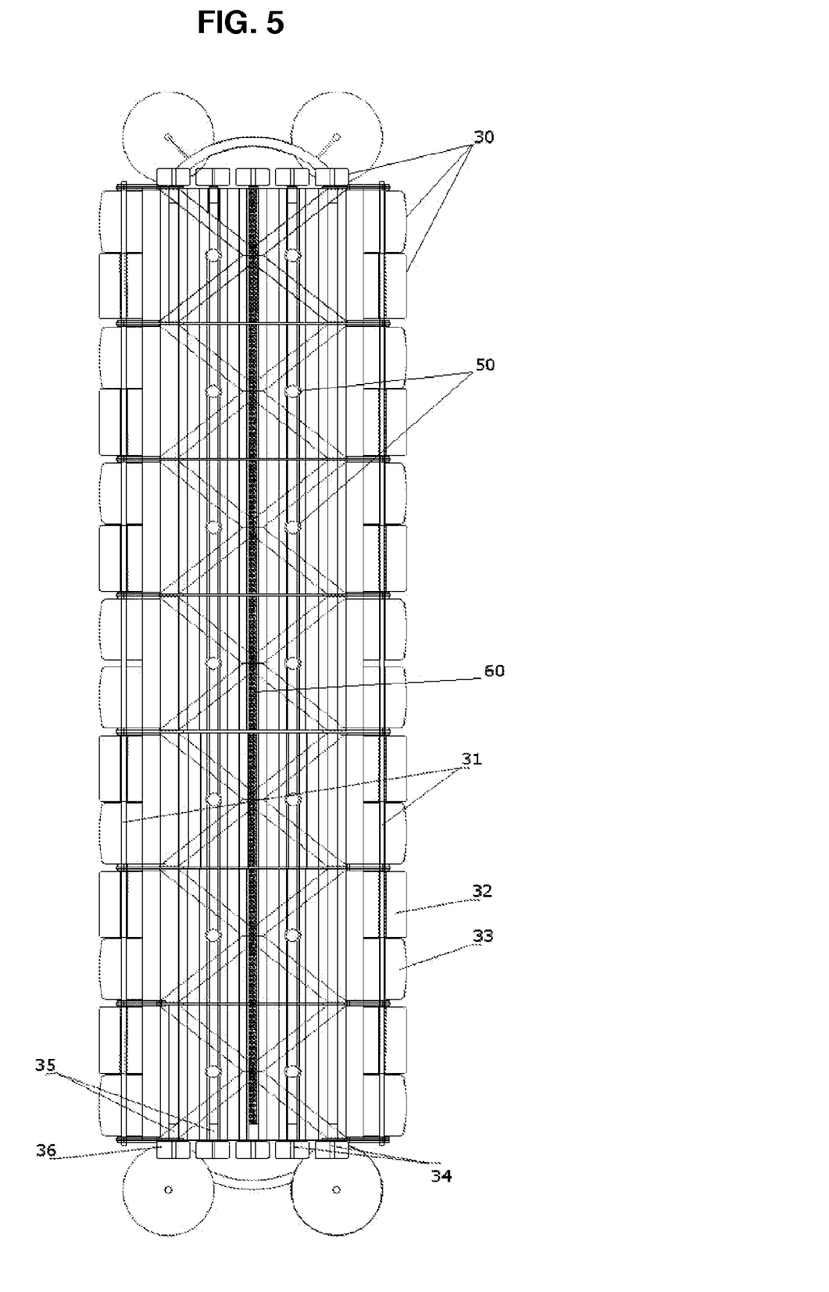
FIG. 5 shows a lower and schematic view of a means of suction with the suctioning device.

As seen in FIG. 5, the means of wheeling (3) comprises stainless steel horizontal axles (31) where semi-rigid polyurethane protective rollers (32) are located, and supporting wheels (33) made of auto-lubricated plastic such as high density polyethylene for the support and displacement of the structural frame (10). Additionally, said means of wheeling (30) comprise secondary axles (34) made of stainless steel in epoxy resin bearings (35) located on the sides of the means of suctioning (50) and means of cleaning (60); in said secondary axles (34) are located secondary wheels (36) made of auto-lubricated plastic such as high density polyethylene for the support and displacement of the means of suctioning (50) and means of cleaning (60). In addition, the means of rotative sliding (40) comprise vertical axles and lateral protective wheels made of auto-lubricated plastic such as high density polyethylene.

Figure 6:
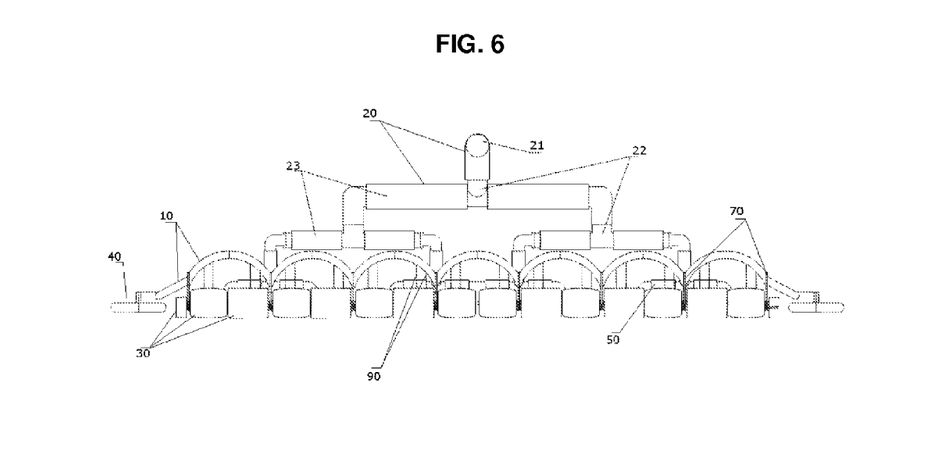
FIG. 6 shows a front view of the suctioning device.

As seen in FIG. 6, the means of coupling (20) comprise a hose nozzle (21) for a flexible hose connected to the pump system, PVC connectors (22) and flexible corrugated pipes (23) which are connected to the means of suctioning and which allow the distribution of suctioning force coming from the pump system.

Figure 7:
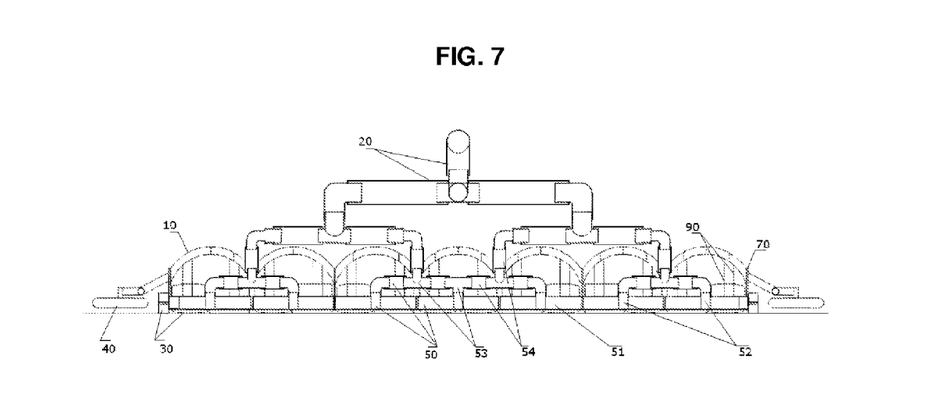
FIG. 7 shows a lower view of the suctioning device.

As seen in FIG. 7, the means of suctioning (5) comprise a folded suctioning channel (51) made of stainless steel which connects suctioning inlets (52) made of stainless steel tubes, argon welded with continuous weld bead to said suctioning channel (51); and PVC connectors (53) and flexible corrugated pipes (54) connected to the means of coupling (20).

Figure 8:
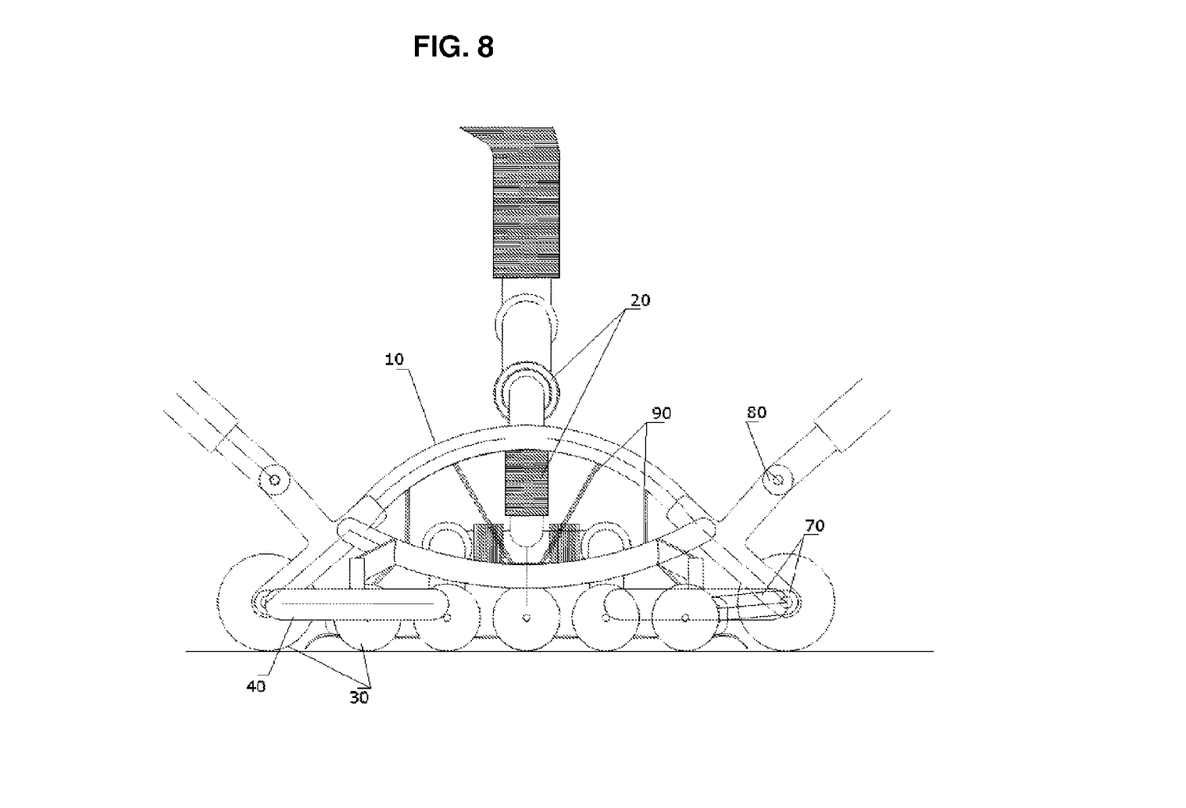
FIG. 8 shows a front view of a longitudinal section of the suctioning device.

As seen in FIG. 8, the means of pivoting (70) connect the structural frame (10), the means of wheeling (30) and the means of suctioning (50) around the horizontal axles (31). Additionally, it is to be pointed out that pivotable means of subjection (80) connect the means of traction (not shown in this Figure) with the structural frame (10).

Figure 9:
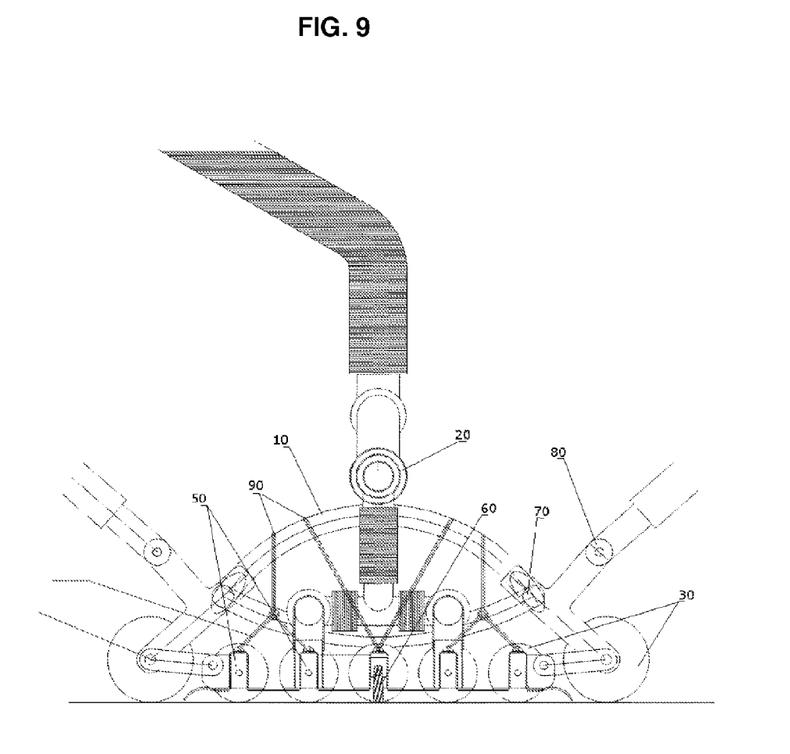
FIG. 9 shows a cross-sectional side view of the suctioning device.

In FIG. 9 it is pointed out that the means of fastening (90) comprise cords, for example, plastic cords, which hang the means of suctioning (50) and means of cleaning (60) on the structural frame (10) at no more than 2 cm from the tank bottom.

Figure 10:
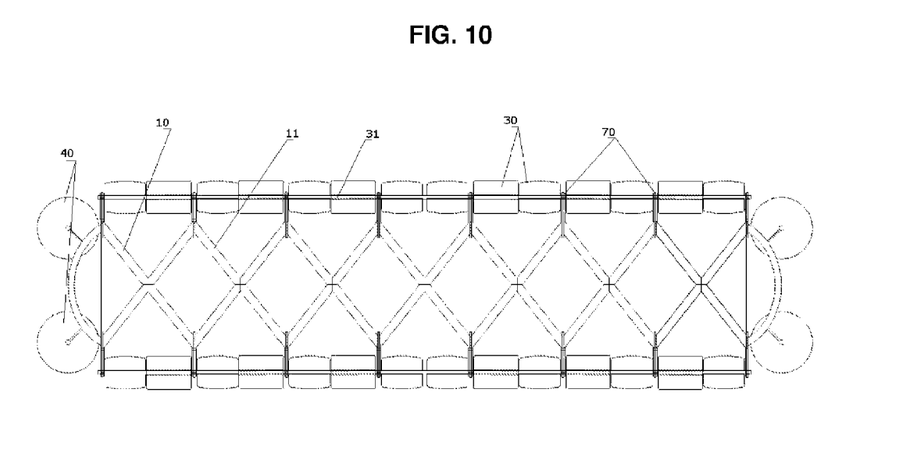
FIG. 10 shows an upper view of a detail of the suctioning device.

As seen in FIG. 10, the structural frame (10) is comprised of intertwined arches (11) for defining an interior space which contains the means of suctioning (50) and means of cleaning (60) hung up by the means of fastening (90). The intertwined arches (11) of the structural frame (10) are fixed by plastic bolts. In the lower ends of said intertwined arches are fixed the means of pivoting (70) which pivot around the horizontal axles (31). Between each supporting wheel (33), protective rollers (32) and secondary wheels (36), as between the means of pivoting (70) and means of pivotable subjection (80), are provided with high density polyethylene washers (not shown in Figures).

Figure 11:
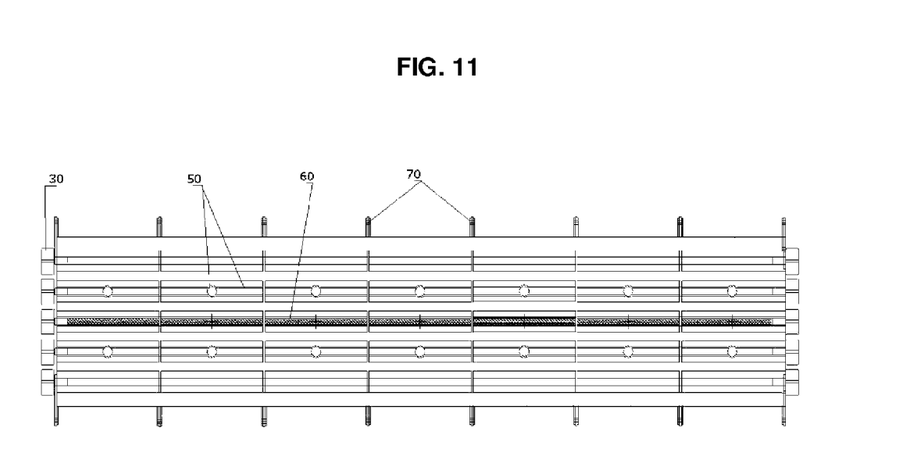
FIG. 11 shows an upper view of an additional detail of the suctioning device.

FIG. 11 shows the distribution of the suctioning inlets (52) in the means of suctioning (50) and means of cleaning (60) as a central brush line.

APPLICATION EXAMPLE

Figure 1:
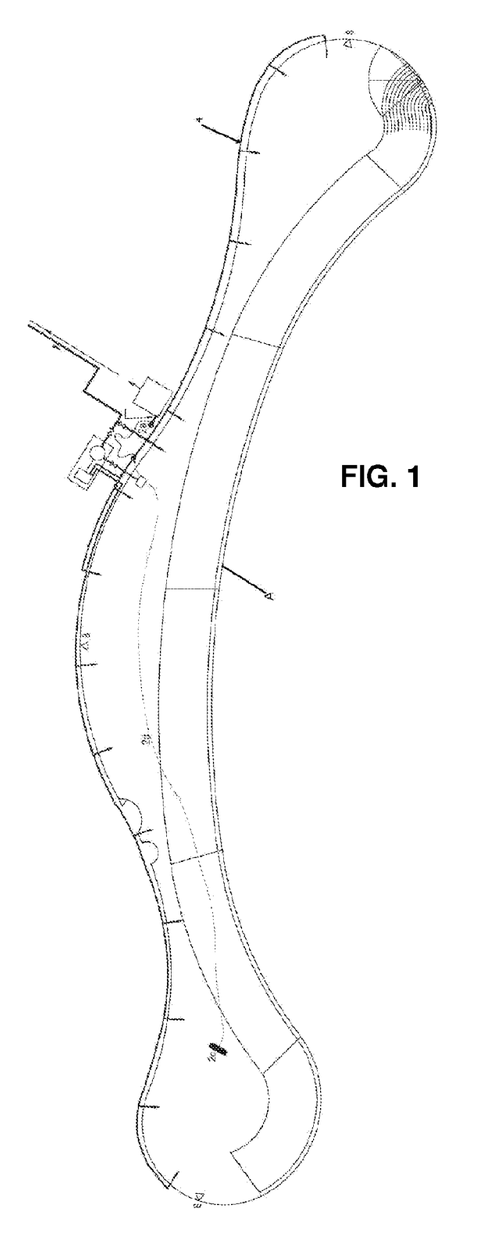
FIG. 1 shows a top view of a tank where the process of the present invention was applied.
Figure 2:
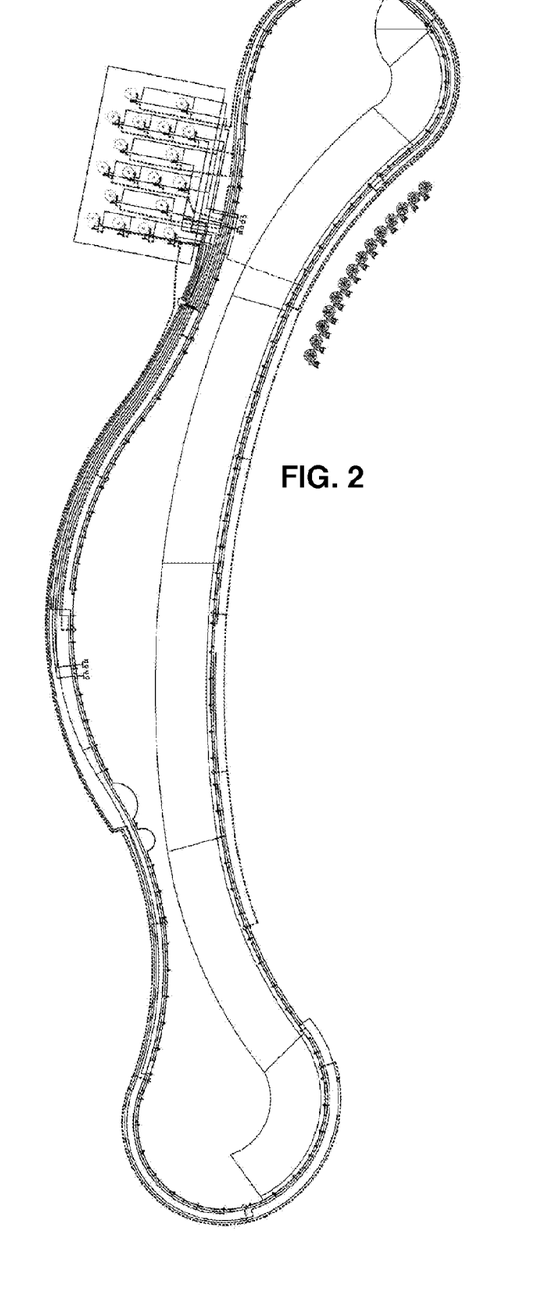
FIG. 2 shows a top view of a tank with a traditional filtration system.

To perform the process of the present invention, which allows efficient filtration of water in tanks such as fountains, reflecting pools, swimming pools and lakes with low investment and operating costs, the following steps were carried out:

A tank (A) was built, similar to an artificial lake, located on the central coast of Chili, (Chile) with an area of approximately 6,000 m$^2$ and a volume of 90,000 m$^3$, as shown in FIG. 1. In FIG. 1 a front view of tank (A) is presented with the necessary structure to perform the process of the present invention. In FIG. 2, a front view of the same tank is shown with the necessary structure to perform traditional filtering, where all of the tank water is filtered. The difference in structure for traditional filtration and filtration according to the process of the present invention can be seen in FIGS. 1 and 2; the structure of FIG. 1 is simpler and more economic than the structure in FIG. 2. In particular, FIG. 2 shows the necessary facilities for traditional filtration, where the great need for tubes for the tank's rims as a filtering area for operating all the necessary filters can be seen. The entire infrastructure needed for traditional filtration can be seen, which generates very high operating and infrastructure costs; on the other hand, FIG. 1 shows the simplicity of the structure needed for a water filtration process according to the present invention and therefore, the economizing in operating and infrastructure costs.

The process of the present invention was performed with the following steps:

In step a), ultrasonic waves were emitted with ultrasonic wave emitting equipment (8), hereafter called a sonicator, trade mark LG Sonics model XL with double frequency in 20 and 100 kHz and 45 W of power, manufactured by LG SOUND, Gerrit van der Veenstraat 752321 CD, Leiden, The Netherlands; with this device the formation of biofilms was prevented and the application of flocculant polymer was reduced by 75%. Said sonicators (8) are located from 10 to 30 cm beneath the water surface using floats and located on the tank rim, as shown in FIG. 1.

Figure 3:
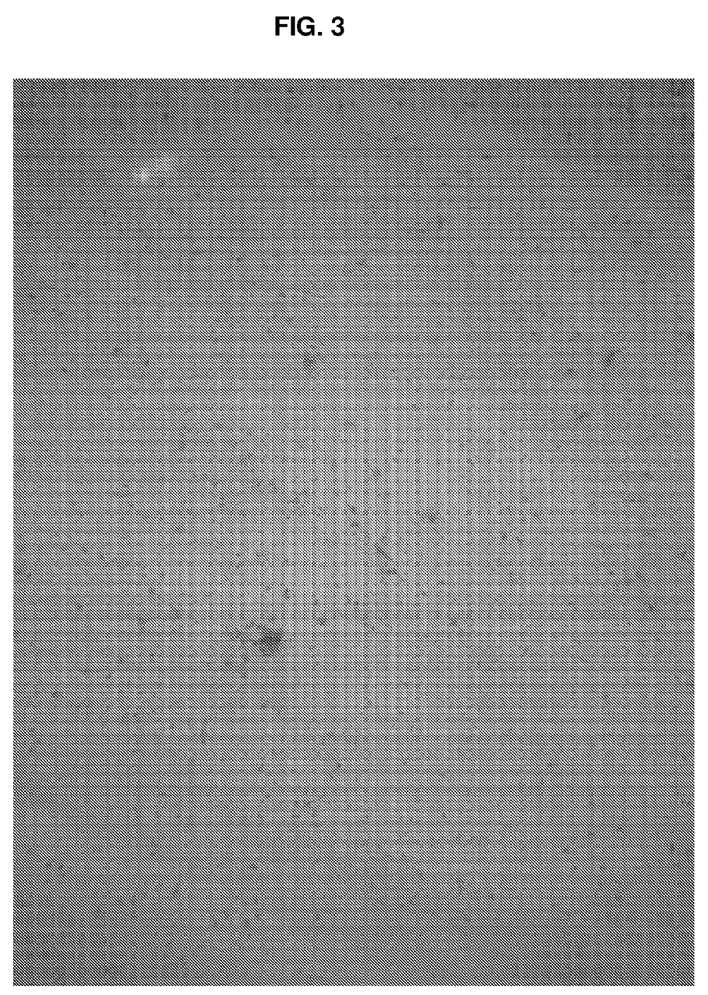
FIG. 3 shows the bottom of a tank, where dispersed floccules due to synergic the effect of ultrasound and flocculant application are observed.

As shown in FIG. 3, the suspended particles were coagulated in a regular form into floccules of a large size which were dispersed, due to the synergic effect between ultrasonic wave emission and flocculant application, which allows an easier suction and efficient filtration of the effluent flow from the suctioning device.

In step b), a cationic polymer was added, Crystal Clear™, which is a biodegradable cationic polyelectrolyte manufactured by AP Aquarium Products, USA, in concentrations of 0.08 ppm every 24 hours.

Figure 4:
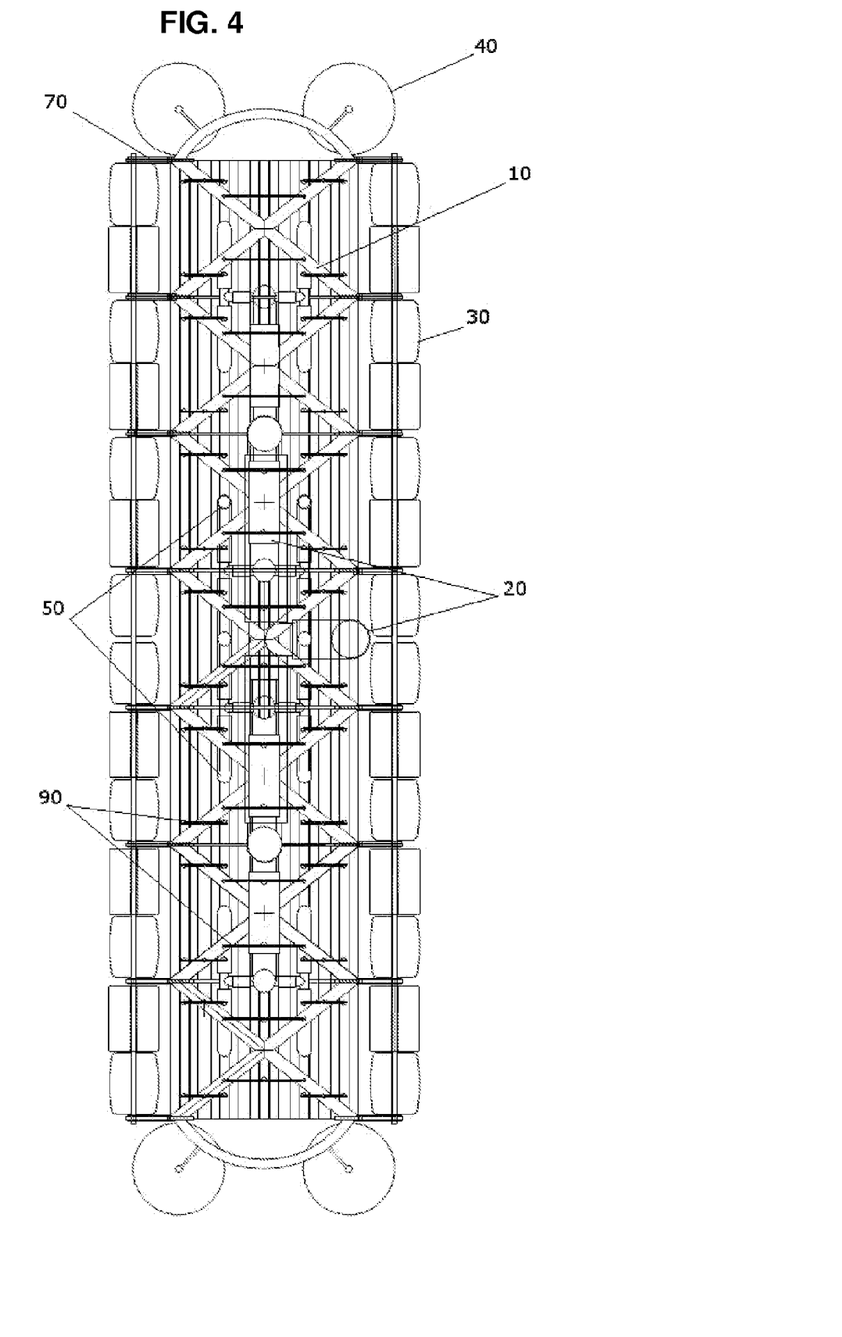
FIG. 4 shows an upper and schematic view of the suctioning device.

In step c), the tank bottom was covered with a suctioning device shown in FIGS. 4 to 6, which captures flocculated particles suctioning a flow of 15 L/s of water with said flocculated particles, for 2 hours every 2 days. As shown in FIG. 1, the effluent from the suctioning device (2c) is suctioned by a mobile pump (2e) with a power of 6.98 kW (9.5 hp) and connected to the suctioning device by a flexible plastic hose (2d) 10.16 cm (4 inches) in diameter and 150 m long, towards a collecting effluent pipe (4), which discharges in several concrete effluent chambers (2a), all of them connected by the collecting effluent pipe (4). Said suctioning device covered the tank bottom, submerged in the tank water and covering a hectare in 3 hours at a speed of 0.93 m/s. Said speed is very superior to that of any similar equipment available on the market. This specially designed device covers at least 100 times more than the surface of the tank bottom, in the same period of time, than any other device available on the market.

In step d), the effluent from the suctioning device was filtered, pumping with a centrifuge pump VOGT®model Serial N 628 of 5.52 kW (7.5 hp) with the force and flow of 15 L/s, connected to a chute 10.16 cm (4 inches) in inner diameter, from one or more concrete effluent chambers. An Aguasin® sand filter model QMA-210-E was used; charged with supporting C-5 gravel and two filtering layers, one of CARENTI C-8 and the other one of CARENIT AN. In step d), of the process of the present invention, the entire effluent was filtered by the suctioning device in an hour and a half, therefore, 15 L/s for 1.5 hour/day was filtered.

In step e), the filtered water was returned to the tank using three recirculating pumps, each with a force of 1.84 kW (2.5 hp) and a flow of 5 L/s, therefore obtaining a recirculation flow of 15 L/s in total.

Biofilms were not formed, therefore the manual cleaning of walls and the suctioning device was not necessary; total turbidity of the water was eliminated and polymer-precipitated impurities were totally eliminated easily and efficiently, leaving the bottom completely clean. The device which suctioned a flow of 15 L/s from the tank bottom, left the tank bottom surface free of particles, floccules and residue layer, as a fine cleaning, different than a simple dredging. The suctioning device was applied to the bottom of the lake for 2 hours every 2 days in order to suction the flow with flocculated particles in the tank bottom, keeping the water completely crystalline, meeting and exceeding the standards for clarity in recreational water in direct contact and the swimming pool regulation of the country of the application embodiment, i.e., Regulation NCh 1333, NCh 209 y Nch. 409.

TABLE 1

Comparative table of treated water with the process of the present invention, compared to the Regulation for recreational water with direct contact NCh 1333 *

| Parameters | Measured Value Pool | NCh 1333 |
|---|---|---|
| pH | 7.8 | 6.5 to 8.3 except if natural conditions of water show different values, but never lower than 5.0 or greater than 9.0 |
| Temperature, ° C., maximum | 17.7 | 30 |
| Clarity, minimum * | 35 meters | Visualization of Secchi discs at 1.20 m of depth |
| Visible floating solids and non natural foams | Absent | Absent |
| Floating oils and fats, mg/l, maximum * | <5 | 5 |
| Emulsified oils and fats, mg/l, maximum * | <5 | 10 |
| Colour, unit scale Pc-Co, maximum * | 10 Absent | 100 Lack of artificial colors |
| Turbidity, silica units, maximum * | 0.55 | 50 |
| Fecal coliform/100 ml, maximum * | — | 1,000 |
| Substances that produce odor or taste problems | Absent | Absent |

* The Chilean official regulations where used (Chili is the country of the application embodiment) Regulation NCh 1333

TABLE 2

Comparative table of treated water with the process of the present invention, compared to the Regulation for pools NCh 209*

| Parameters | Measured Value Pool | NCh 209 |
|---|---|---|
| pH | 7.8 | 7.2-8.2 |
| Residual free chlorine (ppm) | 0.5 | 0.5-1.5 |

TABLE 2-continued

Comparative table of treated water with the process of the present invention, compared to the Regulation for pools NCh 209*

| Parameters | Measured Value Pool | NCh 209 |
|---|---|---|
| Copper (algaecide) (mg/L) | 0.38 | Maximum 1.5 |
| Bromine (desinfectant) (mg/L) | — | 1-3 |
| Foams, fats and suspended particles | Absent | Absent |
| Anaerobic bacteria (colonies/mL) | Absent | ≤200 |
| Fecal coliiforms | Absent | Absent |
| Total coliforms (colonies/100 mL) | Absent | ≤20 |
| Algae, larvae or another live organism | Absent | Absent |
| Visibility of Black Disc of 15 cm | 35 m | 1.4 m |

*The Chilean official regulations where used (Chili is the country of the application example) Regulation NCh209

The filtration of large volumes of water is technically complex and with high costs, and therefore a barrier for the scaling up of crystalline water bodies.

The suctioning device of the present invention eliminates suspended solids flocculated with the flocculant agent and sonication in an efficient and economic way, decreasing the flows to filter by almost 100 times, decreasing the investment in filters, pipes and energy costs during the operation, compared to traditional tank filtration systems. They allow reducing the use of disinfectants, flocculants, algaecides and eliminating biofilms, eliminating the manual cleaning of tank walls and making operation of the suctioning device more efficient.

Besides the high cost, traditional filtration systems do not clean the tank bottom.

The technology described herein, which achieves investment and operating cost reduction remarkably, poses the possibility of eliminating one of the main barriers for building larger crystalline water tanks for recreational and ornamental uses.

The main advantages of the implemented process are the significant energy and chemical product savings, in keeping with protecting the environment and the advantage of investment and maintenance costs which are shown in the following comparative table:

TABLE 3

Comparative table of approximate costs between a traditional filtration system* and the suctioning device

| | Specifications | Circulated volume by pumps | Installation costs | Operation costs, monthly |
|---|---|---|---|---|
| Traditional Filter | 20 VOGT ® centrifuge pumps model Serial N 628, operating with a flow of 15 l/s, with motor of 5.595 kW (7.5 hp) 20 AGUASIN sand filters model QMA-210; 129,600 kg of sand (Carenit C2, C3, C4, C5, C8 y AN); 20 batteries of valves 250 mm; | 300 L/s | US$ 362,180 + | US$ 16,075 |

TABLE 3-continued

Comparative table of approximate costs between a traditional filtration system* and the suctioning device

| | Specifications | Circulated volume by pumps | Installation costs | Operation costs, monthly |
|---|---|---|---|---|
| Process of the invention | Installation workforce; Storehouse of 1,000 m² with special bases for supporting a total weight of 300 tons, with the vibration of filters in operation; 1,998 m. of piping for conduction of water; Total energy used for one month, 24 hours*30 days*20*5.595 kW/hour (80,568 kW/hour) Operators; y Mantainance Windglider Boat Suction pump with motor of 9.5 hp 3 sonicators, model LGSONIC XL Suctioning device Suctioning pump 7.5 hp 449 m of piping for conduction of water 3 recirculating pumps of 1.84 kW (2.5 hp) Hoses, accesories Combustible Flocculant Operator Mantainance | 15 L/s | US$ 18,200 | US$ 910 |

*It is considered T = 4 (Minimum rate for pool filtration) Regulation NCh209
⁺ The cost of land for the storehouse of 1,000 m² is not considered

What is claimed is:

1. A suctioning device for travelling a bottom of a tank containing water, which suctions a water flow with flocculated particles in order to accomplish filtration of the water of said tank, comprising:
 a structural frame having a means of coupling to a pump system, wherein the structural frame comprises at least one cord connected to the structural frame;
 a means of wheeling with a horizontal axle for moving around the bottom of the tank, wherein the means of wheeling are pivotably connected through pivotable connectors to the structural frame so that the means of wheeling are configured to move vertically independent of the structural frame, such that the means of wheeling adapts to prominences in the bottom of the tank;
 a means of rotative sliding with a vertical axle for adjacent displacement to walls of the tank;
 a means of suctioning including a plurality of suction lines; and a means of cleaning;
 wherein the at least one cord fastens the means of suctioning and the means of cleaning to the structural frame.

2. The suctioning device according to claim 1, wherein the structural frame comprises:
 a means of pivotable subjection for attachment to a means of propulsion.

3. The suctioning device according to claim 1, wherein the horizontal axles of the means of wheeling are made of stainless steel and support semi-rigid polyurethane protective rollers, and where supporting wheels made of high density polyethylene for supporting and displacement of the structural frame are located.

4. The suctioning device according to claim 3, wherein the means of wheeling and the means of suctioning are pivotably connected to the structural frame around the horizontal axles.

5. The suctioning device according to claim 4, wherein said means of wheeling further comprises secondary axles made of stainless steel in epoxy resin bearings located on sides of the means of suctioning and means of cleaning, wherein secondary wheels made of high density polyethylene for support and displacement of the means of suctioning and the means of cleaning are located in said secondary axles.

6. The suctioning device according to claim 1, wherein the means of rotative sliding with the vertical axle and further comprising lateral protective wheels made of high density polyethylene.

7. The suctioning device according to claim 1, wherein the means of coupling comprises a hose nozzle for a flexible hose connected to the pump system, PVC connectors and flexible corrugated pipes connected to the means of suctioning.

8. The suctioning device according to claim 1, wherein the means of suctioning comprises:
 a suction channel made of folded stainless steel which connects suctioning inlets made of stainless steel tubes and argon welded to said suctioning channel;
 PVC connectors; and
 flexible corrugated pipes connected to the means of coupling.

9. The suctioning device according to claim 2, wherein the at least one cord hangs the means of suctioning and the means of cleaning on the structural frame no more than 2 cm from the bottom of the tank.

* * * * *